United States Patent [19]

Wang

[11] Patent Number: 4,954,583

[45] Date of Patent: Sep. 4, 1990

[54] ARYLCYCLOBUTENE CARBOXYLATE ESTERS

[75] Inventor: Pen-Chung Wang, Houston, Tex.

[73] Assignee: Shell Oil Company, Houston, Tex.

[21] Appl. No.: 364,275

[22] Filed: Jun. 12, 1989

[51] Int. Cl.$^5$ .............................................. C08G 59/16
[52] U.S. Cl. .................................... 525/507; 528/112;
528/361; 528/365; 528/99; 560/102; 558/426
[58] Field of Search ................ 525/507; 528/112, 361,
528/365, 99; 558/426; 560/102

[56] References Cited

U.S. PATENT DOCUMENTS

| | | | |
|---|---|---|---|
| 3,696,111 | 10/1972 | Juby et al. | 560/102 X |
| 4,371,688 | 2/1983 | Moore | 528/112 |
| 4,451,637 | 5/1984 | Yamato et al. | 528/112 X |
| 4,492,789 | 1/1985 | Nakashima et al. | 528/112 X |
| 4,540,763 | 9/1985 | Kirchhoff | 526/281 |

*Primary Examiner*—Earl Nielsen

[57] ABSTRACT

Novel 1-arylcyclobutenecarboxylate esters of glycidyloxy compounds having at least two glycidyloxy substituents are self-curing thermoset resins. The cured products derived by applying heat to the esters are crosslinked insoluble solids having good properties.

28 Claims, No Drawings

ARYLCYCLOBUTENE CARBOXYLATE ESTERS

FIELD OF THE INVENTION

This invention relates to a novel class of ester derivatives of compounds having two or more glycidyloxy substituents. More particularly, the invention relates to arylcyclobutenecarboxylate derivatives of such glycidyloxy compounds wherein the arylcyclobutene ring system is connected to the remainder of the molecule by a carboxy group substituted on a carbon atom of a cyclobutene ring.

BACKGROUND OF THE INVENTION

The curing of monomeric materials to produce thermoset resins is well known in the art. In general, the polymerizable monomers have at least one and customarily more than one active group which serves as the reactive site for a curing or crosslinking polymerization to produce the thermoset resins which are typically highly crosslinked. The curing or crosslinking of many if not most thermoset resins, for example, the curing of epoxy resins, requires the use of a curing agent, whether catalytic or stoichiometric, to cause the curing or crosslinking reaction to occur at an acceptable rate. Certain other monomers cure in the absence of added curing agent but only upon application of high intensity energy, e.g., ultraviolet (UV) light. Even in the presence of most curing agents the rate of crosslinking is often unduly slow and the addition of an accelerator is generally required to obtain sufficiently rapid curing.

There are some monomers in which the active sites are such that no added curing agent is required and such monomers cure upon application of heat. Such monomers are termed "self-curing". One class of such monomers includes within the molecular structure one or more moieties of an arylcyclobutene, particularly a benzocyclobutene. Such monomers are suitably cured by reaction with a conventional curing agent but also self-cure upon heating in the absence of a curing agent. Without wishing to be bound by any particular theory, it appears probably that upon application of heat the cyclobutene ring undergoes ring opening to produce active intermediates which crosslink by undergoing reaction with adjacent molecules. The resulting cured thermoset resins have properties of rigidity and strength. A series of U.S. patents to Kirchhoff, illustrated by U.S. Pat. No. 4,540,763, describes the production and curing of a large number of benzocyclobutene derivatives, including ethers of bis(hydroxyphenyl)alkanes, wherein the linking group connecting the phenyl of the bis(hydroxyphenyl)alkane to the benzocyclobutene moiety is attached directly to the six-membered ring of the benzocyclobutene. Such monomers are said to be self-curing. In copending U.S. patent application Ser. No. 349,546, filed May 9, 1989, there is described and claimed a class of benzocyclobutenealkyl ethers of bis(hydroxylphenyl)alkanes having a linking group somewhat different from those of Kirchhoff but also attached to the six-membered ring of the benzocyclobutene moiety. These derivatives are also self-curing. It would be of advantage, however, to provide arylcyclobutene derivatives, particularly benzocyclobutene derivatives, having a different link to the remainder of the molecule, i.e., a link from the 4-membered cyclobutene ring of the arylcyclobutene ring system. The resulting monomers crosslink with or without added curing agent to produce cured thermoset resins having good properties.

SUMMARY OF THE INVENTION

This invention relates to a novel class of 1-arylcyclobutenecarboxylate ester derivatives of glycidyloxy compounds having at least two glycidyloxy substituents. More particularly, the invention relates to such arylcyclobutene carboxylates wherein the carboxy linking group is attached to the four-membered ring of the arylcyclobutene ring system. Such ester derivatives are cured through the use of curing agents but are also self-curing thermoset resins. The invention also relates to a method of producing the ester derivatives and to the crosslinked, insoluble, cured product obtained by heating the 1-arylcyclobutenecarboxylate derivatives.

DESCRIPTION OF THE INVENTION

The arylcyclobutenecarboxylate portion of the novel monomeric products of the invention is provided by a 1-arylcyclobutenecarboxylic acid which reacts to open the glycidyl group of the glycidyloxy compounds and produce the esters of the invention at the terminal or gamma carbon atoms of the former glycidyloxy groups. The arylcyclobutenecarboxylic acid is a compound of the formula $A-CO_2H$ wherein the carboxyl group is substituted in the 1-position of a four-membered cyclobutene ring. The arylcyclobutene moiety, A, is an aromatic ring system of up to 4 aromatic rings and up to 30 carbon atoms inclusive which contains at least one cyclobutene ring fused to an aromatic ring. Suitable aromatic ring systems are illustrated by the single aromatic ring system compound benzene, the fused ring system compounds naphthalene, anthracene and phenanthrene, the directly-joined aromatic ring system compounds biphenyl and 1-phenylnaphthalene or the alkylene-joined ring system compounds of two or more aromatic rings joined by an alkylene group, e.g., diphenylalkanes such as diphenylmethane and 2,2-diphenylpropane. The preferred aromatic ring system is a single aromatic ring and the preferred arylcyclobutene moiety is a benzocyclobutene moiety. The arylcyclobutene moiety is hydrocarbyl and is otherwise unsubstituted except for the carboxyl group in the 1-position or is substituted hydrocarbyl containing groups such as cyano in other ring positions, which groups are inert to the conditions under which the reaction of the 1-arylcyclobutenecarboxylate and the glycidyloxy compound takes place. The preferred arylcyclobutenecarboxylic acids are unsubstituted except for the carboxyl group and particularly preferred is 1-benzocyclobutenecarboxylic acid.

The 1-arylcyclobutenecarboxylic acids are known compounds or are produced by known methods. A general review of arylcyclobutene chemistry, particularly benzocyclobutene chemistry, is provided by Klundt, Chemical Reviews, Vol. 70, No. 4, pp. 471–487 (1970) and by the references provided in the review article. By way of a specific preparative example, 1-benzocyclobutenecarboxylic acid is produced by rearrangement of an α-diazaindanone.

The glycidyloxy compounds of the invention are compounds, monomeric or polymeric, which are characterized by the presence within the moleclar structure of at least two glycidyloxy groups, i.e.,

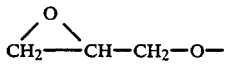

substituents. The glycidyloxy compounds are aromatic including a mixture of aromatic and aliphatic moieties and are hydrocarbyl except for the oxygen atoms of glycidyloxy groups or are substituted hydrocarbyl containing additional atoms in the form of inert carbon atom substituents, e.g., haolgen atoms, preferably middle halogen chloro or bromo, or in the form of inert divalent linking groups connecting portions of the molecule.

The monomeric glycidyloxy compounds have up to 30 carbon atoms and up to 3 aromatic rings, inclusive, and from 2 to 4 glycidyloxy substituents. A preferred class of monomeric glycidyloxy compounds is represented by the formula

(I)

wherein R independently is aromatic of up to 2 aromatic rings and up to 15 carbon atoms, inclusive, X is a direct valence bond, alkylene of up to 20 carbon atoms inclusive, oxy, thio, sulfonyl, carbonyl, dioxyphenylene, i.e.,

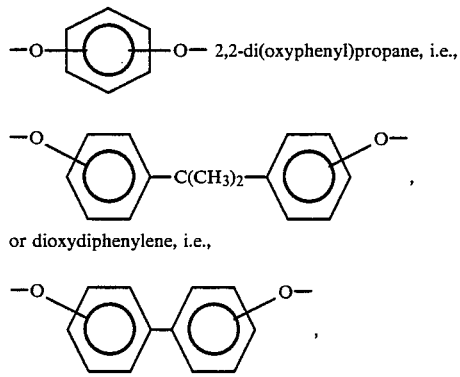

G is glycidyloxy, g independently is 1 or 2 and r is 0 or 1. Preferred R groups have up to 10 carbon atoms, have one aromatic ring and are hydrocarbyl. Particularly preferred R groups are phenylene, especially P-phenylene, and glycidyloxy compounds which are glycidyloxyphenyl compounds.

Illustrative of such monomeric glycidyloxy compounds are 1,4-(diglycidyloxy)naphthalene, di(4-glycidyloxyphenyl) ether, 2,2-di(4-glycidyloxyphenyl)propane, di(3-glycidyloxy-4-methylphenyl) ketone, di(4-glycidyloxyphenyl)methane, 4,4.-di(glycidyloxy)biphenyl, 1-[4,5-di(glycidyloxy)naphthyl]4-glycidyloxyphenyl sulfone, 3,3',5-triglycidyloxybiphenyl and di(4-glycidyloxy-2-chlorophenyl)methane.

In general, compounds of the above formula 1 are preferred wherein each of g and r are 1 and X is alkylene, oxy, sulfonyl or carbonyl. Particularly preferred are the di(glycidyloxyphenyl)alkanes, i.e., X is alkylene, particularly alkylene of up to 8 carbon atoms, inclusive, especially 2,2-di(4-glycidyloxyphenyl)propane.

The monomeric glycidyloxy compounds are known compounds or are produced by known methods. For example, a glycidyloxy compound is produced from the corresponding hydroxy compound by reaction with a stoichiometric quantity of epichlorohydrin and a base, particularly an alkali metal base. Certain of the glycidyloxy compounds, particularly 2,2-di(4-glycidyloxyphenyl)propane, are commercial products used in the production of certain epoxy resins.

The polymeric glycidyloxy compounds which are useful as precursors of the esters of the invention are oligomers, i.e., low molecular weight polymers, having moieties derived from an epihalohydrin and a hydroxyphenylalkane. In one modification, the oligomer is produced by reaction of a molar excess of an epihalohydrin such as epichlorohydrin and a di(hydroxyphenyl)alkane to prepare glycidyl ethers of hydroxyphenylalkane moieties joined by hydroxypropane ether or by other groups. Such oligomers occur in a number of structural types but are well known in the art. In one class of such oligomers, the oligomer is an alternating oligomer characterized by alternating di(oxyphenyl)alkane and 2-hydroxy-1,3-propylene moieties and is capped with glycidyl groups, for example, the oligomers of the formula

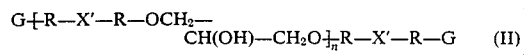
(II)

wherein G and R have the previously stated meanings and X is alkylene of up to 20 carbon atoms inclusive, preferably up to 8 carbon atoms. The term n is an integer from 1 to about 40, preferably from 1 t° about 20. It will be appreciated that within a given oligomer sample there will be oligomer molecules which will have differing values for n so that, on average, n is not necessarily a whole number. A particularly preferred class of the oligomers of formula 11 are those produced from epichlorohydrin and 2,2-di(4-hydroxy phenyl)propane. Such oligomers are depicted by the above formula II wherein each R is p-phenylene and each X is Z,Z-propylene.

The production of these oligomers is conventional and well known in the art and is illustrated by the disclosures of Locatelli, U.S. Pat. No. 4,269,952, Alber et al, U.S. Pat. No. 4,306,054, and Wsng et al, U.S. Pat. No. 4,499,255. A number of the oligomers are commercial and are marketed by Shell Chemical Company under the trademark EPON@ Epoxy Resin.

In an alternate, although generally less preferred, embodiment of the polymeric glycidyloxy compounds of the invention the oligomers are polyglycidyl ethers of a poly(hydroxyphenylalkane). These oligomers are represented by the glycidyl ethers of the poly(hydroxyphenylalkanes) commonly referred to as Novolac resins. The glycidyl derivatives of such resins are illustrated by the formula

(III)

where G, R, X' and n have the previously stated meanings. A preferred class of such derivatives of these Novolac resins are those of the above formula III wherein R is o-phenylene and X' is methylene.

The Novolac-type resins are produced by conventional procedures from a phenol and an alkehyde, frequently formaldephyde, or cyclic dienes such as dicyclopentadiene. The disclosure of Speranza et al, U.S. Pat. No. 4,102,866 is illustrative. The glycidyl ethers are produced from the resins by the methods described above.

To produce the novel arylcyclobutene derivatives of the invention, the 1-arylcyclobutenecarboxylic acid and the glycidyloxy compound are preferably employed in substantially stoichiometric quantities, that is, about 1 mole of arylcyclobutenecarboxylic acid for each mole of glycidyloxy group present in one mole of the glycidyloxy compound of at least two glycidyloxy substituents. However, reactant ratios of moles of arylcyclobutenecarboxylic acid to mole of glycidyloxy groups from about 4:1 to about 1:2 are satisfactory.

The reaction is conducted in the substantial absence of reaction diluent when the reactants are liquid and reaction conditions or in the presence of an inert reaction diluent such as toluene in the case where one or both of the reactants is solid at reaction temperature and pressure. A satisfactory reaction rate is most easily obtained if the reaction of the 1-arylcyclobutenecarboxylic acid and the glycidyloxy compound are contacted in the presence of a catalyst. Quaternary phosphonium halides or quaternary ammonium halides have been found to be satisfactory as catalyst, particularly tetra(hydrocarbyl)phosphonium or tetra(hydrocarbyl)ammonium halides wherein at least one of the hydrocazbyl substituents is phenyl or alkyl with any other substituents being alkyl, particularly lower alkyl, and the halide is a middle halide, i.e., chloride or bromide. Illustrative of such phosphonium or ammonium halides are trimethylphenylphosphonium chloride, ethyltriphenylphosphonium bromide, tetrabutylammonium bromide, di-n-butyldiphenylphosphonium bromide and tetraphenylphosphonium chloride. Alkyltriphenylphosphonioum halides are preferred, especially ethyltriphenylphosphonium bromide. The phosphonium halide is employed in a catalytic quantity. Amounts of phosphonium halide from about 1% by weigh to about 10% by weight, based on total reactants, are satisfactory with amounts from about 2% by weight to about 6% by weight on the same basis being preferred.

The reaction is conducted by intimately contacting the arylcyclobutenecarboxylic acid reactant, the glycidyloxy compound reactant, the catalyst and any diluent to be employed and maintaining the mixture under reaction conditions. An elevated reaction temperature is generally utilized and reaction temperatures from about 30° C. to about 200° C. are satisfactory with reaction temperatures from about 50° C. to about 150° C. being preferred. The reaction pressure to be employed is a pressure which is sufficient to maintain the reaction mixture in a liquid phase. Such pressures are typically up to about 10 atmospheres but more often are from about 0.8 atmospheres to about 5 atmospheres.

Subsequent to reaction, the desired arylcyclobutenecarbpxylate derivative is obtained from the product mixture. If desired, the ester product is separated and purified by convntional methods such as selective extraction, precipitation or solvent removal. Particularly in the embodiment of the invention where the reactions are employed in substantially stoichiometric ratios without the utilization of added diluent the product is obtained in sufficiently high conversion and selectivity so as to allow its use in most applications without the need for purification.

The ester products of the invention are novel 1-arylcyclobutenecarboxylate esters of the glycidyloxy compound illustratively produced by opening of the glycidyl rings with formation of a hydroxy substituent on the center carbon atoms of the three-carbon former glycidyloxy substituent and an ester linkage from the arylcyclobutene moiety to the terminal carbon atom. In terms of the monomeric glycidyloxy derivatives of formula I, the products are illustrated by the formula

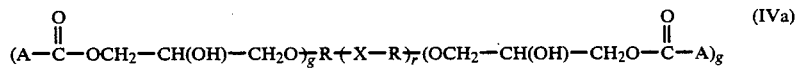

(IVa)

wherein A, R, X, g and r have the previously stated meanings. In terms of the polymeric glycidyloxy compounds of formulas 11 and III, the products are illustrated by the formula

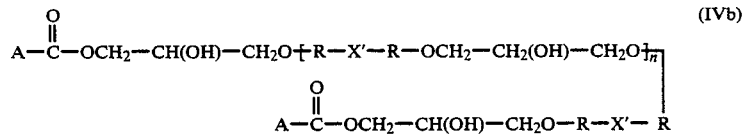

(IVb)

or by the formula

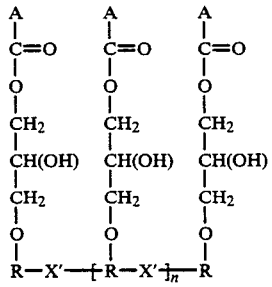

(IVc)

respectively, where A, R, X' and n have the previously stated meanings. The nomenclature of the products, particularly the polymeric products, is difficult because of the complexity thereof. By way of specific illustration, however, the product of 1-benzenecyclobutenecarboxylic acid and 2,2-di(4-hydroxyphenyl)propane is 2,2-di[4-(3-oxy-2-hydroxypropyloxy)- phenyl]propane di(1-benzocyclobutenecarboxylate). The identity of other products will be apparent from consideration of the above formula for the reactants and the products.

The arylcyclobutenecarboxylate esters of the bis(-glycidyloxy) compounds are generally low melting solids or viscous liquids. Although the esters will react easily with curing agents, the esters are self-curing and will cure or crosslink without the presence of added curing agent or accelerator by heating the ester to a temperature above about 100° C., preferably from about 150° C. to about 250° C. The cured products are rigid thermosets with a highly crosslinked structure and good physical strength. The esters are processed by methods which are conventional for curing monomeric compounds by application of heat. The cured products find utility as structural coating materials in aerospace and electronic applications.

The reaction of the esters with certain curing agents is described and claimed in copending U.S. patent application Ser. No. 364,276 filed June 12, 1989 together with the cured products thereby obtained.

The invention is further illustrated by the following Illustrative Embodiments which should not be regarded as limiting.

ILLUSTRATIVE EMBODIMENT I

A mixture of 29.6 g (0.2 mole) 1-benzocyclobutenecarboxylic acid, 34.0 g (0.1 mole) of 2,Z-bis(4-glycidyloxyphenyl)propane and 0.3 g of ethyltriphenylphosphonium bromide was stirred at 50° C. for 2 hours and at 100° C. for an additional 12 hours. The resulting product,

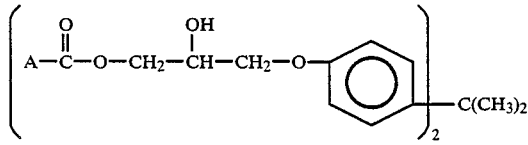

was obtained in a yield greater than 99%. The identity of the product was confirmed by $^{13}$C-NMR analysis which was consistent with the above structure.

ILLUSTRATIVE EMBODIMENT II

The ester product of Illustrative Embodiment I was heated at 200° C. for 2 hours and at 220° C. for an additional 4 hours. The resulting product was a crosslinked, insoluble material having a glass transition temperature of 121° C.

What is claimed is:

1. A 1-arylcyclobutenecarboxylate ester of a glycidyloxy compound wherein the arylcyclobutene moiety has up to 4 aromatic rings and up to 30 carbon atoms and has at least one cyclobutene ring fused to an aromatic ring, and the glycidyloxy compound has at least two glycidyloxy substituents.

2. The ester of claim wherein glycidyloxy compound is represented by the formula

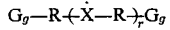

wherein G is glycidyloxy, R is aromatic of up to 15 carbon atoms and up to 2 aromatic rings, inclusive, X is a direct valence bond, alkylene of up to 20 carbon atoms inclusive, oxy, thio, sulfonyl, carbonyl, dioxyphenylene, 2,2-di(oxyphenyl)propane or dioxydiphenylene, and g independently is 1 or 2 and r is 0 or 1.

3. The ester of claim 2 wherein the arylcyclobutene moiety is benzocyclobutene.

4. The ester of claim 3 wherein X is alkylene, oxy, sulfonyl or carbonyl.

5. The ester of claim 4 wherein X is alkylene.

6. The ester of claim 5 wherein R is p-phenylene and X is 2,2-propylene.

7. The ester of claim 1 wherein the glycidyloxy compound is represented by the formula

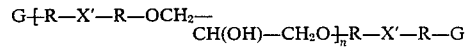

wherein G is glycidyloxy, R is aromatic of up to 15 carbon atoms and up to 2 aromatic rings, inclusive, and n is an integer from 1 to about 40.

8. The ester of claim 7 wherein the arylcyclobutene moiety is benzocyclobutene.

9. The ester of claim 8 wherein X is 2,2-propylene and R is p-phenylene.

10. The ester of claim 1 wherein the glycidyloxy compound is represented by the formula

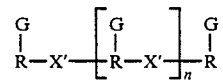

where G is glycidyloxy, R is aromatic of up to 15 carbon atoms and up to 2 aromatic rings, inclusive, X' is alkylene of up to 20 carbon atoms inclusive, and n is an integer from 1 to about 40.

11. The ester of claim 10 wherein the arylcyclobutene moiety is benzocyclobutene.

12. The ester of claim 11 wherein X' is methylene and R is o-phenylene.

13. The crosslinked insoluble solid obtained by heating the ester of claim 1 to a temperature above about 100° C.

14. The crosslinked insoluble solid obtained by heating the ester of claim 6 to a temperature above about 100° C.

15. The process of producing an 1-arylcyclobutenecarboxylate acid ester of a glycidyloxy compound by contacting under reaction conditions (a) 1-arylcyclobutenecarboxylic acid wherein the arylcyclobutene moiety has up to 4 aromatic rings and up to 30 carbon atoms inclusive, and has at least one cyclobutene ring fused to an aromatic ring, and (b) an aromatic glycidyloxy compound compound having at least two glycidyloxy substituents, in the presence of a quaternary phosphonium halide catalyst.

16. The process of claim 15 wherein glycidyloxy compound is represented by the formula

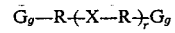

wherein G is glycidyloxy, R is aromatic of up to 15 carbon atoms and up to 2 aromatic rings, inclusive, X is a direct valence bond, alkylene of up to 20 carbon atoms inclusive, oxy, thio, sulfonyl, carbonyl, dioxyphenylene, 2,2-di(oxyphenyl)propane or dioxydiphenylene, and g independently is 1 or 2 and r is 0 or 1.

17. The process of claim 16 wherein the arylcyclobutene moiety is benzocyclobutene.

18. The process of claim 17 wherein X is alkylene, oxo, sulfonyl or carbonyl.

19. The process of claim 18 wherein R is p-phenylene, g is 1 and r is 1.

20. The process of claim 19 wherein X is 2,2-propylene.

21. The process of claim 15 wherein the glycidyloxy compound is represented by the formula

wherein G is glycidyloxy, R is aromatic of up to 15 carbon atoms and up to 2 aromatic rings, inclusive, X' is alkylene of up to 20 carbon atoms inclusive, and n is an integer from 1 to about 40.

22. The process of claim 21 wherein the arylcyclobutene moiety is benzocyclobutene.

23. The process of claim 22 wherein X is 2,2-propylene.

24. The process of claim 23 wherein R is p-phenylene.

25. The process of claim 15 wherein the glycidyloxy compound is represented by the formula

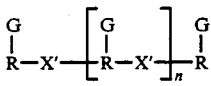

where G is glycidyloxy, R is aromatic of up to 15 carbon atoms and up to 2 aromatic rings, inclusive, X' is alkylene of up to 20 carbon atoms inclusive, and n is an integer from 1 to about 40.

26. The process of claim 25 wherein the arylcyclobutene moiety is benzocyclobutene.

27. The process of claim 26 wherein X is methylene.

28. The process of claim 27 wherein R is o-phenylene.

* * * * *